United States Patent [19]

Martin

[11] Patent Number: 4,479,961
[45] Date of Patent: Oct. 30, 1984

[54] SYNERGISTIC FUNGICIDE/BIOCIDE OF 2-(THIOCYANOMETHYLTHIO) BENZOTHIAZOLE AND BIS (TRICHLOROMETHYL) SULFONE

[75] Inventor: Cynthia H. Martin, Joliet, Ill.

[73] Assignee: Nalco Chemical Company, Oak Brook, Ill.

[21] Appl. No.: 573,264

[22] Filed: Jan. 23, 1984

[51] Int. Cl.$^3$ .................. A01N 31/00; A01N 41/10
[52] U.S. Cl. ................................. 424/270; 424/337
[58] Field of Search ................................ 424/270

[56] References Cited

U.S. PATENT DOCUMENTS 3,426,134  2/1969  Shema et al. .................. 424/337

OTHER PUBLICATIONS

Chemical Abstracts, vol. 73 (1970); Anon.; #546916 "Food Additives, Slimicides".

*Primary Examiner*—Leonard Schenkman
*Assistant Examiner*—Joesph A. Lipovsky
*Attorney, Agent, or Firm*—John G. Premo; Robert A. Miller; Donald G. Epple

[57] ABSTRACT

Synergistic combinations of 2-(thiocyanomethylthio) benzothiazole and bis (trichloromethyl) sulfone are effective in controlling the growth of fungi and bacteria. Effective use of synergistic combinations of the two chemicals mentioned above can be made in industrial waters such as recirculating cooling waters or waters used for producing pulp papers and paper products.

17 Claims, No Drawings

SYNERGISTIC FUNGICIDE/BIOCIDE OF 2-(THIOCYANOMETHYLTHIO) BENZOTHIAZOLE AND BIS (TRICHLOROMETHYL) SULFONE

INTRODUCTION

The present invention relates to certain processes and compositions useful for inhibiting and controlling the growth of both microbiological and fungal matter such as bacteria, yeast and molds, and, specifically, for controlling the growth of the fungi, *Aspergillus niger* and *Saccharomyces cerevisiae*, and the bacteria, *Pseudomonas aeruginosa*. The novel compositions and methods for controlling bacterial and fungal growth, yeast and mold growth, and particularly the growth of the specific fungi and bacteria mentioned above are derived by combining two specific ingredients in effective weight ratios and adding an effective amount of these combinations to medias which contain the micro organisms which cause such bacterial and fungal growth. The two specific ingredients found most effective in controlling this fungal growth are bis (trichloromethyl) sulfone and 2-(thiocyanomethylthio) benzothiazole.

The haloalkyl sulfones utilized in the practice of this invention are primarily the bis (trichloromethyl) sulfone disclosed in U.S. Pat. Nos. 2,959,517 and 3,051,757. The 2-(thiocyanomethylthio) benzothiazole is also a known biocide referred to as TCMTB-1030 and is available commercially.

These compositions are useful for controlling bacterial and fungal growth, the growth of various yeast and mold organisms, and, specifically, for controlling the growth of the fungi and bacteria mentioned above, when used within a weight ratio of the substituted sulfone to substituted benzothiazole ranging between about 10/90 to about 90/10.

The use of the synergistic combination of substituted sulfone and substituted benzothiazole is particularly effective in industrial waters such as recirculating cooling water systems, waters used in the manufacture of paper, pulp paper and paper products, and waters used in the textile industry. The use of these synergistic combinations is particularly beneficial when applied to industrial waters used in the manufacture of pulp papers since the formation of bacterial and fungal slimes from bacteria, yeast, and mold deposits can adversely effect the quality of the final paper product as well as the manufacturing rate at which the product is made.

PRIOR ART

The combination of other biocidal compounds with substituted halodimethyl sulfones have previously been described in U.S. Pat. Nos. 3,231,509, 3,426,134, 3,896,231, 3,929,561, and 3,989,585. However, none of these U.S. patents describes the specific combination of bis (trichloromethyl) sulfone with 2-(thiocyanomethylthio) benzothiazoles. It is this last combination of ingredients which comprises the compositions of this invention, and it is the use of these effective synergistic compositions which is the object of the method for controlling bacterial and fungal growth described below.

THE INVENTION

My invention is a composition for controlling bacterial and fungal growth, the growth of yeast and mold organisms, and, specifically, for controlling the growth of the micro-organisms, *Pseudomonas aeruginosa*, *Aspergillus niger* and *Saccharomyces cerevisiae*. The compositions found effective for controlling this bacterial and fungal growth, yeast and mold growth, and the specific micro-organisms mentioned above comprises a combination of bis (trichloromethyl) sulfone and 2-(thiocyanomethylthio) benzothiazole. The trihalomethyl sulfone to thiocyanomethylthio benzothiazole weight ratios preferred to obtain the synergistic results required for the effective use of this combination ranges between a weight ratio of substituted sulfone to substituted benzothiazole ranging between 10/90 to 90/10.

This synergistic combination of ingredients may be added to industrial water samples at concentrations ranging between 0.3 to 50 ppm based on an active amount of the combined ingredients.

The synergistic combination of ingredients reviewed above may be added to industrial water samples within a pH range between about 2.5 and about 9.5 while still maintaining efficacious results. A bacterial toxicity study using the ingredients of this invention demonstrated a preferred toxicity level at pH's ranging between about 3.5 and about 7.0. As industrial waters become more basic, that is, have increased pH's above 7.0, some of the toxicity levels for these micro-organisms can be lost. However, this activity is not entirely lost and synergistic results are still anticipated.

The range of pH in which these synergistic microbiocide and microfungicide ingredients may be effectively used is between about 2.5 pH units and about 9.5 pH units. The preferred water pH at which synergistic results are obtained ranges between about 3.5 and about 8.5. The most preferred range is between about 4.0 and about 7.0.

EXAMPLES

The synergism of these two components is demonstrated by adding 2-(thiocyanomethylthio) benzothiazole and bis (trichloromethyl) sulfone in varying ratios over a range of concentrations to liquid nutrient medium. For the study of fungal growth control, the liquid nutrient medium chosen was a potato dextrose agar, which was poured into sterile Petri dishes and allowed to solidify. Each test plate was then inoculated with a fungal suspension containing both *Aspergillus niger* and *Saccharomyces cerevisiae*. After 5, 10, and 14 day incubations at 30° C., the lowest concentration of each ratio of the substituted benzothiazole and substituted sulfone that prevented growth on the agar medium was taken as the end points.

The end points for each of the ratios tested were then compared with end points for the pure active ingredients working alone. Synergism was determined by the method described by S. C. Kull, P. C. Eisman, H. D. Sylwestrowicz, and R. L. Mayer as reported in *Applied Microbiology*, Vol. 9, pages 538–541, (1936), which is incorporated herein by reference.

In the Kull, et al. reference, the following description can be applied to the data presented in Tables I and II which follow:

$Q_A$ = quantity of TCMTB-1030, acting alone, producing an endpoint;

$Q_a$ = quantity of TCMTB-1030, in the mixture, producing an endpoint;

$Q_B$ = quantity of sulfone, acting alone, producing an endpoint;

$Q_b$ = Quantity of sulfone, in the mixture, producing an endpoint, $$\text{if } \frac{Q_a}{Q_A} + \frac{Q_b}{Q_B} < 1 \text{ is synergism}$$

$$> 1 \text{ is antagonism}$$

$$= 1 \text{ is additivity}$$

Test Parameters

Nutrient medium: potato dextrose agar
Test organisms: *Aspergillus niger, Saccharomyces cerevisiae*
Incubation: 14 days at 30° C. (plates read at 5, 10, and 14 days)
Ratios of TCMTB-1030/sulfone: 100/0, 0/100, 90/10, 10/90, 50/50, 75/25, 25/75
Concentrations of each ratio on an active basis in parts per million: 0.3, 0.6, 1.0, 1.5, 3.0, 5.0, 7.5, 10, 20, 30, 40, 50.

TABLE I

Synergism Study for Combination Fungicide

Growth: +
No Growth: −
Inoculum Culture: 2.0 × 10⁵ organisms per 0.1 milliliter yeast
1.0 × 10⁴ organisms per 0.1 milliliter mold

| Ratio TCMTB-1030/ Sulfone | Concentration (ppm): | | | | | | | | | | | |
|---|---|---|---|---|---|---|---|---|---|---|---|---|
| | 0.3 | 0.6 | 1.0 | 1.5 | 3.0 | 5.0 | 7.5 | 10 | 20 | 30 | 40 | 50 |
| 100/0 | | | | | | | | | | | | |
| Yeast | + | + | + | + | − | − | − | − | − | − | − | − |
| Mold | + | + | + | + | + | − | − | − | − | − | − | − |
| 0/100 | | | | | | | | | | | | |
| Yeast | + | + | + | + | + | + | + | + | + | + | + | + |
| Mold | + | + | + | + | + | + | + | + | + | + | + | + |
| 90/10 | | | | | | | | | | | | |
| Yeast | + | + | + | + | − | − | − | − | − | − | − | − |
| Mold | + | + | + | + | − | − | − | − | − | − | − | − |
| 10/90 | | | | | | | | | | | | |
| Yeast | + | + | + | + | + | + | + | − | − | − | − | − |
| Mold | + | + | + | + | + | + | + | − | − | − | − | − |
| 50/50 | | | | | | | | | | | | |
| Yeast | + | + | + | + | − | − | − | − | − | − | − | − |
| Mold | + | + | + | + | − | − | − | − | − | − | − | − |
| 75/25 | | | | | | | | | | | | |
| Yeast | + | + | + | + | − | − | − | − | − | − | − | − |
| Mold | + | + | + | + | − | − | − | − | − | − | − | − |
| 25/75 | | | | | | | | | | | | |
| Yeast | + | + | + | + | + | − | − | − | − | − | − | − |
| Mold | + | + | + | + | + | − | − | − | − | − | − | − |

Calculations
$Q_A$ for yeast = 3.0 parts per million active
$Q_A$ for mold = 5.0 parts per million active
$Q_B$ for yeast and mold = 50 parts per million active Calculations $Q_A$ for yeast = 3.0 parts per million active
$Q_A$ for mold = 5.0 parts per million active
$Q_B$ for yeast and mild = >50 parts per million active A. 90/10 for yeast:
$Q_a$ = 3.0 ppm × .90 = 2.7 ppm
$Q_b$ = 3.0 ppm × .10 = .3 ppm $$\frac{2.7}{3.0} + \frac{.3}{>50} = 0.9 + <.006 = <0.906$$

90/10 for mold:

$$\frac{2.7}{5.0} + \frac{.3}{>50} = .54 + <.006 = <.546$$

B. 10/90 for yeast:
$Q_a$ = 10 ppm × .10 = 1 ppm
$Q_b$ = 10 ppm × .90 = 9 ppm $$\frac{1}{3} + \frac{9}{>50} = .33 + <.18 = <.51$$

10/90 for mold:

$$\frac{1}{5} + \frac{9}{>50} = .2 + <.18 = <.38$$

C. 50/50 for yeast:
$Q_a$ = 3.0 ppm × .50 = 1.5 ppm
$Q_b$ = 3.0 ppm × .50 = 1.5 ppm $$\frac{1.5}{3.0} + \frac{1.5}{>50} = .5 + <.03 = <.53$$

50/50 for mold:

$$\frac{1.5}{5.0} + \frac{1.5}{>50} = .3 + <.03 = <.33$$

D. 75/25 for yeast:
$Q_a$ = 3.0 ppm × .75 = 2.25 ppm
$Q_b$ = 3.0 ppm × .25 = .75 ppm $$\frac{2.25}{3.0} + \frac{.75}{>50} = .75 + <.015 = <.765$$

75/25 for mold:

$$\frac{2.25}{5.0} + \frac{.75}{>50} = .45 + <.015 = <.465$$

E. 25/75 for yeast:
$Q_a$ = 5.0 ppm × .25 = 1.25 ppm
$Q_b$ = 5.0 ppm × .75 = 3.75 ppm $$\frac{1.25}{3.0} + \frac{3.75}{>50} = .416 + <.075 = <.491$$

25/75 for mold:

$$\frac{1.25}{5.0} + \frac{3.75}{>50} = .25 + <.075 = <.325$$

TABLE II

| Ratio TCMTB 1030/ Sulfone | Yeast $\frac{Q_a}{Q_A} + \frac{Q_b}{Q_B}$ | Synergistic Additive Antagonistic | Mold $\frac{Q_a}{Q_A} + \frac{Q_b}{Q_B}$ | Synergistic Additive Antagonistic |
|---|---|---|---|---|
| 90/10 | <.906 | <1 synergerstic | <.546 | <1 synergistic |
| 10/90 | <.51 | <1 synergistic | <.38 | <1 synergistic |
| 50/50 | <.53 | <1 synergistic | <.33 | <1 synergistic |
| 75/25 | <.765 | <1 synergistic | <.465 | <1 synergistic |
| 25/75 | <.491 | <1 synergistic | <.325 | <1 synergistic |

As can be seen by close examination of the data, the combination of bis (trichloromethyl) sulfone with 2-(thiocyanomethylthio) benzothiazole at weight ratios of 90/10, 10/90, 50/50, 75/25, and 25/75 results in synergistic activity in regards to controlling fungal growth, yeast and mold growth, and particularly the specific combination of the micro-organisms, *Aspergillus niger* and *Saccharomyces cerevisiae*. This synergistic combination of chemicals within the weight ratio range between 10/90 and 90/10 has better activity in controlling fungal growth than does the activity of either the substituted sulfone or substituted benzothiazole when used alone.

These effective synergistic compositions can, therefore, be used in a method for controlling fungal growth which comprises adding an effective amount of a combination of bis (trichloromethyl) sulfone and 2-(thiocyanomethylthio) benzothiazole wherein the weight ratio of substituted sulfone to substituted benzothiazole ranges between 10/90 to about 90/10. An effective amount of this synergistic composition can be as low as 0.3 ppm active composition of the combined ingredients used within the industrial waters to be treated. It would be expected that the addition of this effective amount of the synergistic composition mentioned above may be added to industrial waters which are recirculating cooling waters at a concentration of at least 0.3 ppm.

Likewise, a method for controlling fungal growth in industrial waters which comprises adding thereto an effective amount of a combination of ingredients mentioned above is anticipated wherein the industrial waters or waters are used in the manufacture of pulp papers and paper products.

In a similar manner, a bacterial synergism study was undertaken to demonstrate the synergism of the two components described above in varying ratios over a range of concentrations when added to a liquid nutrient medium on which a nutrient broth culture of *Pseudomonas aeruginosa* had been inoculated. The liquid nutrient medium was composed of a Tryptone Glucose Extract Agar maintained at approximately 37° C. The treated agar was poured into sterile Petri dishes, allowed to solidify, and then inoculated with 0.1 milliliters of a nutrient broth culture of *Pseudomonas aeruginosa*.

After 48 hours incubation at 37° C., the lowest concentration of each ratio that prevented growth on the agar medium was taken as the end point. End points for each of the ratios were compared with end points for the pure active ingredients working alone, and synergism was again determined by the method described by Kull, et al.

The test parameters and results are summarized below:

Test Parameters

Nutrient Medium: Tryptone Glucose Extract Agar
Test Organisms: *Pseudomonas aeruginosa*

Calculations $Q_A = 10$ ppm active TCMTB
$Q_B = 10$ ppm active Sulfone

A. 90/10 Ratio:

$Q_a = 0.90 \times 5$ ppm $= 4.5$ ppm $Q_b = 0.10 \times 5$ ppm $= 0.5$ ppm $$\frac{4.5 \text{ ppm}}{10 \text{ ppm}} + \frac{0.5 \text{ ppm}}{10 \text{ ppm}} = 0.50$$

B. 75/25 Ratio:

$Q_a = 0.75 \times 5$ ppm $= 3.75$ ppm $Q_b = 0.25 \times 5$ ppm $= 1.25$ ppm $$\frac{3.75 \text{ ppm}}{10 \text{ ppm}} + \frac{1.25 \text{ ppm}}{10 \text{ ppm}} = 0.50$$

-continued

C. 50/50 Ratio:

$Q_a = 0.50 \times 5$ ppm $= 2.5$ ppm $Q_b = 0.50 \times 5$ ppm $= 2.5$ ppm $$\frac{2.5 \text{ ppm}}{10 \text{ ppm}} + \frac{2.5 \text{ ppm}}{10 \text{ ppm}} = 0.50$$

D. 25/75 Ratio:

$Q_a = 0.25 \times 7.5$ ppm $= 1.875$ ppm $Q_b = 0.75 \times 7.5$ ppm $= 5.625$ ppm $$\frac{1.875 \text{ ppm}}{10 \text{ ppm}} + \frac{5.625 \text{ ppm}}{10 \text{ ppm}} = 0.75$$

E. 1090 Ratio:

$Q_a = 0.10 \times 5$ ppm $= 0.5$ ppm $Q_b = 0.900 \times 5$ ppm $= 4.5$ ppm $$\frac{0.5 \text{ ppm}}{10 \text{ ppm}} + \frac{4.5 \text{ ppm}}{10 \text{ ppm}} = 0.50$$

TABLE III

BACTERIAL SYNERGISM STUDY FOR COMBINATION BIOCIDE

Growth: +
No Growth: —
Inoculum Culture: $5.6 \times 10^7$ organisms per 0.1 milliliter

| Ratio TCMTB/ Sulfone | 2 | 5 | 7.5 | 10 | 15 | 20 | 30 | 40 | 50 | 60 | 70 | 80 | 90 | 100 |
|---|---|---|---|---|---|---|---|---|---|---|---|---|---|---|
| 100/0 | + | + | + | — | — | — | — | — | — | — | — | — | — | — |
| 0/100 | + | + | + | — | — | — | — | — | — | — | — | — | — | — |
| 90/10 | + | — | — | — | — | — | — | — | — | — | — | — | — | — |
| 75/25 | + | — | — | — | — | — | — | — | — | — | — | — | — | — |
| 50/50 | + | — | — | — | — | — | — | — | — | — | — | — | — | — |
| 25/75 | + | + | — | — | — | — | — | — | — | — | — | — | — | — |
| 10/90 | + | — | — | — | — | — | — | — | — | — | — | — | — | — |

TABLE IV

| Ratio TCMTB/Sulfone | Bacteria $\frac{Q_a}{Q_A} + \frac{Q_b}{Q_B}$ | Synergistic Additive Antagonistic |
|---|---|---|
| 90/10 | 0.50 | Synergistic |
| 75/25 | 0.50 | Synergistic |
| 50/50 | 0.50 | Synergistic |
| 25/75 | 0.75 | Synergistic |
| 10/90 | 0.50 | Synergistic |

As again can be seen by close examination of this data, the combination of bis (trichloromethyl) sulfone with 2-(thiocyanomethylthio) benzothiazole at weight ratios ranging between 90/10 to 10/90 result in synergistic activity in regards to controlling bacterial growth from the *Pseudomonas aeruginosa* bacilli. This synergistic combination of chemicals within the weight ratios above mentioned has better activity for controlling this bacterial growth than does the individual ingredients, the substituted sulfone or substituted benzothiazole, when used separately and alone. These effective synergistic compositions can, therefore, be used in a method for controlling both bacterial growth and fungal growth which comprises adding an effective amount of a combination of bis (trichloromethyl) sulfone and 2-(thiocyanomethylthio) benzothiazole wherein the weight ratio of substituted sulfone to substituted benzothiazole ranges between 10/90 to about 90/10. An effective amount of this synergistic composition can be as low as 0.3 ppm active composition of the combined ingredients used within the industrial waters to be treated. It would be expected that the addition of this effective amount of synergistic composition mentioned above may be added to industrial waters which are recirculating cooling waters at a concentration of at least 0.3 ppm to control both the growth of bacterial contaminants as well as prevent the growth of fungal contaminants.

Similarly, a method of controlling bacterial and fungal growth in industrial waters which comprises adding thereto an effective amount of a combination of ingredients mentioned above is anticipated to serve those industries wherein the industrial waters are used in the manufacture of pulp papers and paper products.

I claim:

1. A composition for controlling bacterial and fungal growth which comprises a combination of bis (trichloromethyl) sulfone and 2-(thiocyanomethylthio) benzothiazole wherein the weight ratio of sulfone to benzothiazole ranges between 10/90 to 90/10.

2. A method for controlling bacterial and fungal growth which comprises adding to a media containing said growth at least 0.3 parts per million of a combination of bis (trichloromethyl) sulfone and 2-(thiocyanomethylthio) benzothiazole wherein the weight ratio of sulfone to benzothiazole ranges between 10/90 to 90/10.

3. A method of controlling the growth of the fungi, *Aspergillus niger*, and *Saccharomyces cerevisiae* which comprises adding to a media containing said fungi at least 0.3 parts per million of a combination of bis (trichloromethyl) sulfone and 2-(thiocyanomethylthio) benzothiazole wherein the weight ratio of sulfone to benzothiazole ranges between 10/90 to 90/10.

4. A method of controlling the growth of bacteria, yeast, and mold, either separately or in combination, which comprises adding at least 0.3 parts per million of a combination of bis (trichloromethyl) sulfone and 2-(thiocyanomethylthio) benzothiazole wherein the weight ratio of sulfone to benzothiazole ranges between 10/90 to 90/10.

5. A method of controlling bacterial and fungal growth in industrial waters which comprises adding thereto at least 0.3 parts per million of a combination of bis (trichloromethyl) sulfone and 2-(thiocyanomethylthio) benzothiazole wherein the weight ratio of sulfone to benzothiazole ranges between 10/90 to 90/10.

6. The method of claim 5 wherein the industrial waters are recirculating cooling waters.

7. The method of claim 5 wherein the industrial waters are waters used in the manufacture of pulp papers.

8. A method of controlling bacterial growth which comprises adding to a media containing said growth at least 0.3 parts per million of a combination of bis (trichloromethyl) sulfone and 2-(thiocyanomethylthio) benzothiazole wherein the weight ratio of sulfone to benzothiazole ranges between 10/90 to 90/10.

9. A method of controlling fungal growth which comprises adding to a media containing said growth at least 0.3 parts per million of a combination of bis (trichloromethyl) sulfone and 2-(thiocyanomethylthio) benzothiazole wherein the weight ratio of sulfone to benzothiazole ranges between 10/90 to 90/10.

10. A composition for controlling bacterial growth which comprises a combination of bis (trichloromethyl) sulfone and 2-(thiocyanomethylthio) benzothiazole wherein the weight ratio of sulfone to benzothiazole ranges between 10/90 to 90/10.

11. A composition for controlling the growth of the bacilli, *Pseudomonas aeruginosa* which comprises a combination of bis (trichloromethyl) sulfone and 2-(thiocyanomethylthio) benzothiazole wherein the weight ratio of sulfone to benzothiazole ranges between 10/90 to 90/10.

12. The method of controlling bacterial and fungal growth of claim 5 which comprises controlling the pH of the industrial waters within a range between 2.5–9.5.

13. The method of claim 5 wherein the industrial waters are controlled within a pH range between 2.5–9.5.

14. The method of claim 6 wherein the recirculating cooling waters have a controlled pH within the range of 2.5–9.5.

15. The method of claim 14 wherein the recirculating cooling waters have a controlled pH within the range of 4.0–7.0.

16. The method of claim 7 wherein the industrial waters used in the manufacture of pulped papers are controlled within the pH range between 2.5–9.5.

17. The method of claim 16 wherein the pH range is between 4.0–7.0.

* * * * *